United States Patent [19]

Grant

[11] 4,051,205

[45] Sept. 27, 1977

[54] APPARATUS FOR SATURATED GAS DELIVERY

[76] Inventor: Graham Cameron Grant, 16149 Campbell Parade, Manly Vale 2093, Sydney, New South Wales, Australia

[21] Appl. No.: 612,149

[22] Filed: Sept. 10, 1975

Related U.S. Application Data

[63] Continuation-in-part of Ser. No. 396,032, Sept. 10, 1973, abandoned.

[30] Foreign Application Priority Data

Sept. 13, 1972 Australia .............................. 0427/72
Nov. 17, 1972 Australia .............................. 1267/72

[51] Int. Cl.² ...................... A61M 15/00; B01F 15/06
[52] U.S. Cl. ..................................... 261/70; 128/192; 219/272; 219/275; 219/276; 261/119 R; 261/130; 261/142; 261/153; 261/DIG. 65
[58] Field of Search ........... 261/142, 152, 153, 119 R, 261/130, 70, DIG. 65, 66; 128/186, 188, 192-194; 219/271-273, 275, 276, 311, 362, 307, 306; 215/222; 248/74 A, 74 B

[56] References Cited

U.S. PATENT DOCUMENTS

| 353,311 | 11/1886 | Keller ............................. 261/70 X |
| 2,111,206 | 3/1938 | Coe ............................. 261/DIG. 65 |
| 3,171,889 | 3/1965 | McCarthy ...................... 248/74 B X |
| 3,434,471 | 3/1969 | Liston ............................. 128/192 X |
| 3,456,598 | 7/1969 | MacKay ......................... 261/142 X |
| 3,638,926 | 2/1972 | Melville et al. ................. 261/130 |
| 3,659,604 | 5/1972 | Melville et al. ............. 261/DIG. 65 |
| 3,806,102 | 4/1974 | Valenta et al. ............. 261/DIG. 65 |
| 3,820,540 | 6/1974 | Hirtz et al. ................. 261/DIG. 65 |
| 3,864,440 | 2/1975 | Giocoechea ................. 261/DIG. 65 |

FOREIGN PATENT DOCUMENTS

| 656,683 | 5/1929 | France .............................. 261/119 R |
| 576,213 | 11/1930 | Germany .............................. 261/142 |

Primary Examiner—Tim R. Miles
Assistant Examiner—Richard L. Chiesa
Attorney, Agent, or Firm—Ladas, Parry, Von Gehr, Goldsmith & Deschamps

[57] ABSTRACT

Apparatus for humidifying a gas stream comprises a transparent reservoir having a top cap and connected via a float controlled valve chamber beneath to a humidifying chamber. The valve maintains a desired water level in the humidification chamber which has a heated floor and gas inlet and outlet ports in its top. Gas flowing between the ports is humidified to a figure approaching 80% and has its temperature raised to a higher temperature than is required at a point of use. The humidified gas flows through a hose which controls the cooling of the humidified gas so that 100% saturation cannot occur until the gas reaches the outlet of the delivery hose at the point of use. The temperatures of the hose and humidification chamber are separately controlled by their own control loops. The float chamber, reservoir and humidification chamber are made of the transparent material and the float and humidification chambers share a common metallic base which is readily detachable for cleaning.

9 Claims, 10 Drawing Figures

APPARATUS FOR SATURATED GAS DELIVERY

CROSS REFERENCE TO RELATED APPLICATION

This application is a continuation-in-part of an application filed in the U.S. Patent Office on Sept. 10, 1973, Ser. No. 396,032 for METHOD AND APPARATUS FOR VAPOUR SATURATED GAS DELIVERY, now abandoned in favor of a continuation application, Ser. No. 611,382 filed Sept. 8, 1975.

BACKGROUND OF THE INVENTION

This invention relates to the delivery of temperature and vapour level controlled gases to a delivery point.

The invention has particular, but non-exclusive, application in relation to humidifiers for use in the medical field and it is herein described for convenience of reference in this context.

When a normal person breathes atmospheric air his air passages supply heat and moisture to the inhaled gases, the body being capable of supplying the required amount of heat and moisture. However under certain conditions in medical practice a patient's mechanism of supplying heat and moisture is interfered with, and it becomes necessary to provide an artificial means for warming inspired gases to a point at or near normal body temperature (37° C) before the gas is delivered to the patient. Similarly, it is necessary to humidify the inspired gases to a level at or near full (100%) saturation.

Temperature and vapour level controlled air might typically be required to be delivered to a shocked or very ill patient, to a patient whose air passages have been bypassed by a tube or tracheotomy for artificial ventilation, to a neonatal patient (who has a low reserve of heat and moisture) undergoing intensive care, or to a patient who is subject to prolonged breathing of cylinder stored compressed gases.

Apparatus which is currently employed for the conditioning of gases to be delivered to a patient generally takes the form of either a so-called nebuliser or a heated humidifier. Nebulisers function to produce fine water droplets in a heated gas suspension, by a process of atomisation but they are known to have serious disadvantages. Heated humidifiers function by supplying heat and moisture to a gas by the passage of the gas through or over a heated waterbath or evaporative surface.

The heated humidifier type apparatus is currently manufactured in one or other of two forms (vis., a simple humidifier or a heated hose humidifier), but each has its characteristic disadvantages. In the simple humidifier gases are saturated with water vapour by being passed over heated water within a tank humidifier chamber and are then fed to a patient by way of a flexible hose. Considerable heat losses to atmosphere occur during passage of the gas through the hose and, in order to obtain a delivery temperature at or near body temperature, it is necessary to heat the water in the humidification chamber to a much higher temperature than that required by the patient. This results in heavy condensation along the hose length and, unless the condensate is cleared from the system a potentially hazardous situation is created.

To overcome this problem heated hose humidifiers have been developed in which the delivery hose is itself heated to maintain the temperature of gases delivered from the humidifying chamber above the dewpoint. In this case the chamber is operated at a constant temperature which corresponds to that required by the patient and as the hose is heated to a slightly higher temperature, condensation within the hose is avoided. However, it is characteristic of such apparatus that the humidifier itself is run at or near normal body temperature and because a simple tank humidifier will not produce vapour at above approximately 80% saturation at the gas flows involved, a much larger than normal evaporative surface inside the tank is required. This has involved the use of a complicated structure to provide the necessary evaporative surface inside the tank and such a structure is inevitably relatively difficult to service and clean.

It is an object of this invention to provide a gas conditioning apparatus employing a humidifier tank which is easier to service and clean than prior art apparatus.

SUMMARY OF THE INVENTION

In its broadest aspect the invention provides conditioning apparatus comprising a reservoir chamber, a float chamber located beneath said reservoir chamber, a valve between said reservoir and float chambers, a float in said float chamber operatively controlling liquid flow through said valve, a humidifying chamber surrounding said float chamber, means permitted equalizing of liquid levels in said float chamber and said humidifying chamber, a gas entry port leading into the upper portion of said humidifying chamber, a humidified gas exit port remote from said gas entry port and leading from the upper portion of said humidifying chamber, a flexible hose leading from said gas exit port, a heating element extending along said flexible hose, a gas temperature sensing element located at the gas outlet end of said hose, first electrical connections extending from said temperature sensing element, second electrical connections extending from said heating element, a temperature sensor in said humidifying chamber, third electrical connections extending from said sensor, a stand, a heater in said stand for heating said humidifying chamber, control circuitry having inputs receiving the first, second and third connections respectively and controlling operation of the hose heating element and said heater, independently operating closed loop control circuits of which the first controls the hose heating element in response to the output of the temperature sensor and the second controls the heater in response to the output of the temperature sensing element, and alarm circuitry monitoring the first and second control loops and providing a warning if, for any reason, during operation of the apparatus, any of a number of predetermined hazard conditions develops.

A simple humdifier tank structure of the invention is easy to clean, sterilize, and assemble. In use, the humidifier does not itself need to produce full saturation this being achieved by controlling the temperature drop along the line.

The invention will be more fully understood from the following description of preferred embodiments thereof taken in conjunction with the accompanying drawings wherein.

DESCRIPTION OF THE PREFERRED EMBODIMENTS

Figure 1:
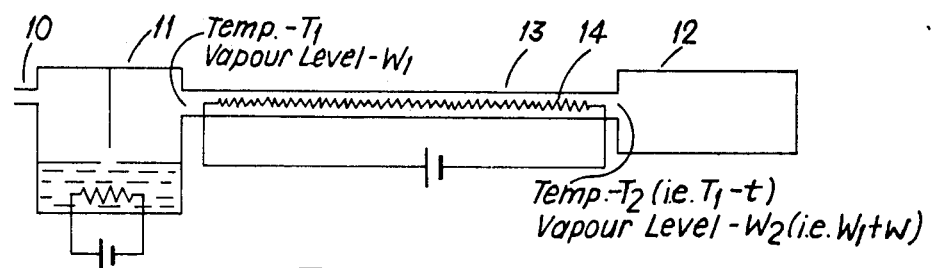
FIG. 1 is a schematic representation of the broad principal of the invention.

As shown in FIG. 1, a gas such as air or oxygen is delivered by way of a conduit 10 to a heated tank type humidifier 11, at which the vapour level of the gas is raised to a desired level, and the gas is passed from the humidifier to a delivery point 12, typically a patient, via a flexible delivery line 13.

The humidifier 11 is controlled to provide for vapour saturation of the gas to a level $W_1$ less than 100% R.H. and, typically, to a level of 80–90% saturation. Also, the humidifier provides for heating the vapour to a temperature $T_1$ which is higher than a temperature $T_2$ required of the gas upon its delivery to the patient.

Then, to provide for delivery of the gas to the patient at a (desired) higher vapour level $W_2$, typically at full saturation, the temperature along the delivery line is controlled to give the lower temperature $T_2$ at the delivery point. Temperature control is effected in order to offset losses along the delivery line by locating a resistance heater 14 along the line.

The above described method of controlling the temperature vapour level of a gas is utilised in the two humidifying apparatuses shown in the remaining figures of the drawings. However, before proceeding with a description of the illustrated apparatuses it is noted that, in the interest of convenience and economics, a single humidifier should be suitable for both adult and paediatric use, and to meet this requirement the following criteria must be satisfied: (a) For adults, the surface area of evaporation must be large enough to provide for high level saturation at large gas flows, and the capacity of a water reservoir, forming part of the humidifier tank must be sufficiently large as to avoid the need for constant refilling. (b) For infants, the compression volume of the reservoir should be as small as possible when using a mechanical respirator so as to reduce the compliance of the circuit as much as possible.

A simple humidifying tank cannot be used to meet these two seemingly conflicting requirements at the same time and it has been appreciated by the inventor that it is necessary to provide the humidifier with a water reservoir separated from an evaporating chamber, and to maintain a constant water level within the evaporating chamber by feeding the chamber with water from the reservoir when required. The evaporating chamber can then be kept quite small, in the interest of preserving a low gas compression volume. However, if there is direct communication between the reservoir and the evaporating chamber nothing will be gained, because the air within the reservoir might still be compressed.

In the apparatus described, a valve is provided which closes during the compression (inspiratory) phase but which operates to let water pass from the reservoir as required during the expiratory phase. In general use the valve also gives rise to the following advantages:

a. an evaporation chamber of constant and small compression volume, independent of water level in the reservoir;

b. a greater storage volume of water is thus possible, reducing the frequency of need for refilling. The upper reservoir has a capacity such that, with a minute volume of 10 liters (patient), it will last approximately 12 hours;

c. a clearly visible water level in the upper chamber and a reserve of water in the lower chamber even when the upper chamber is empty, so that there is a safety margin if exhaustion of water in the reservoir is not immediately noticed;

d. the humidifier may be refilled at any time from the top without having to break the patient circuit as in existing humidifiers. When used with a respirator the valve automatically closes during the compression phase; and, e. when refilling the reservoir there is no need to observe a specific upper water level as in existing humidifiers.

Figure 2:
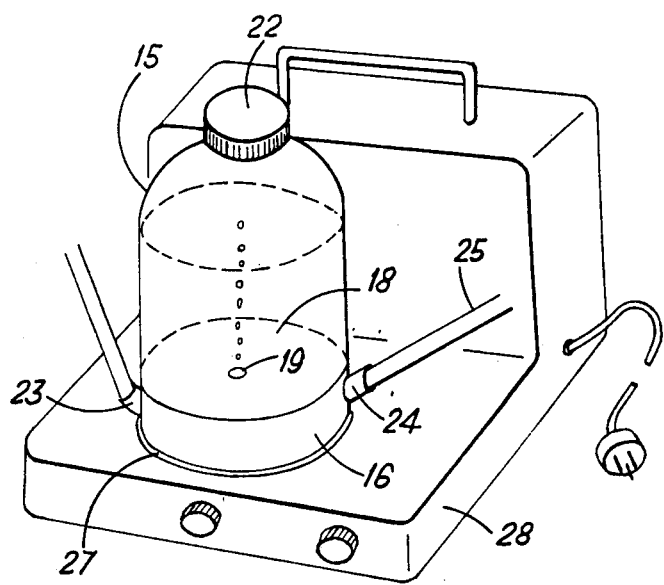
FIG. 2 is a perspective view of a humidifying apparatus for use in medical applications and which embodies the invention.
Figure 3:
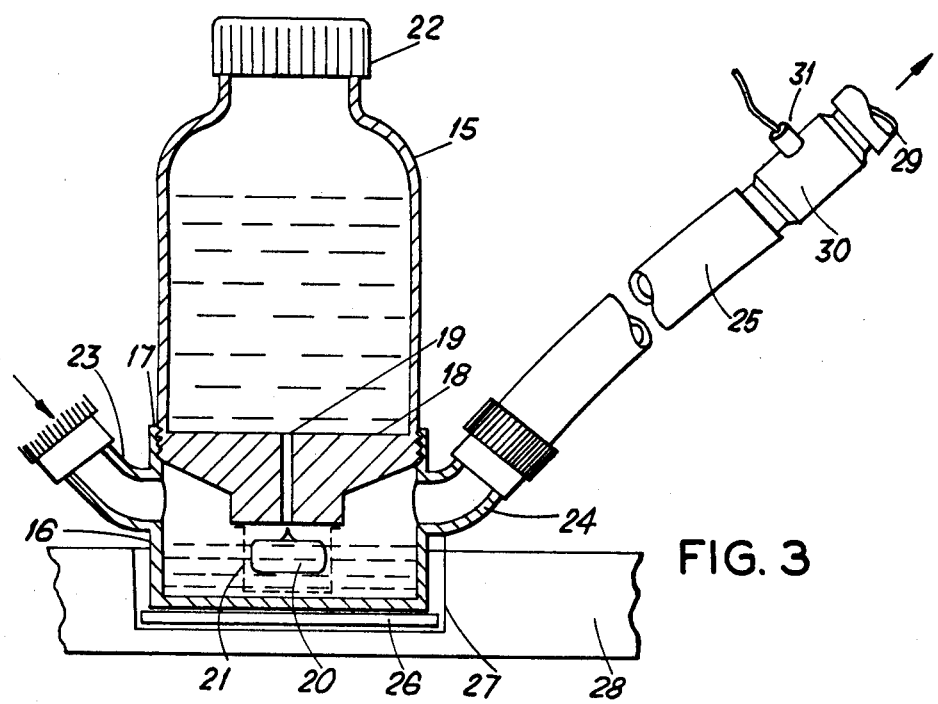
FIG. 3 is an elevation view, partially in cross section, of a portion of the humidifying apparatus.

As shown in FIGS. 2 and 3, the apparatus comprises a reservoir 15 which is mounted above an evaporating chamber 16, the two being screw connected at 17.

The lower end of the reservoir is formed with a base 18, and the reservoir communicates with the evaporating chamber 16 by way of a port 19. A desired water level is maintained within the evaporating chamber by a float-supported valve 20 which is located within a cage portion 21 of the reservoir base.

The float 20 serves to maintain an optimum level in the evaporating chamber and to seal against the port 19 when the water level in the chamber 16 rises or when there is gas compression in the chamber, during an inspiratory phase when a mechanical respirator is used.

An air-tight cap 22 closes the reservoir, so that if the float 20 should fail, the water level in the evaporating chamber will be prevented from rising above the level of the lower end of the port and thereby obstruct the respiratory circuit. The cap 22 also seals the reservoir against air-borne bacteria. Also, a fail-safe high/low water sensor device (not shown) is incorporated in the evaporating chamber 16.

Gases to be heated and humidified are directed into the chamber 16 by way of an inlet port 23, and the heated, humidified gases pass from the chamber by way of an exit port 24 and delivery line 25.

Heat transfer to the water within the chamber 16 and to gases passing through the chamber is effected by way of a heating coil 26 upon which the evaporating chamber normally sits. The heating coil is located within a pocket portion 27 of a casing 28 which serves to house control gear associated with the humidifier. The necessary temperature control circuitry is hereinafter described with reference to FIG. 4 of the drawings.

The delivery line 25 is constituted by a flexible plastics hose which has a helical form electrical resistance element (14 see FIG. 1) embedded in its wall, and the resistance element functions as a secondary heater, as above described with reference to FIG. 1. Also, the delivery line 25 is connected to, for example, an endotracheal tube connector 29 by way of a coupling 30. The coupling 30 is fitted within its interior with a sensor 31, such as a thermister or platinum resistance element, which is wired to the control circuitry. The sensor serves to detect the temperature level of gas passing from the delivery line to the patient and thus to provide an error signal to enable controlled regulation of electrical energy, applied to the resistance element 14 to occur so that the delivered gas temperature remains sensibly constant.

Figure 4:
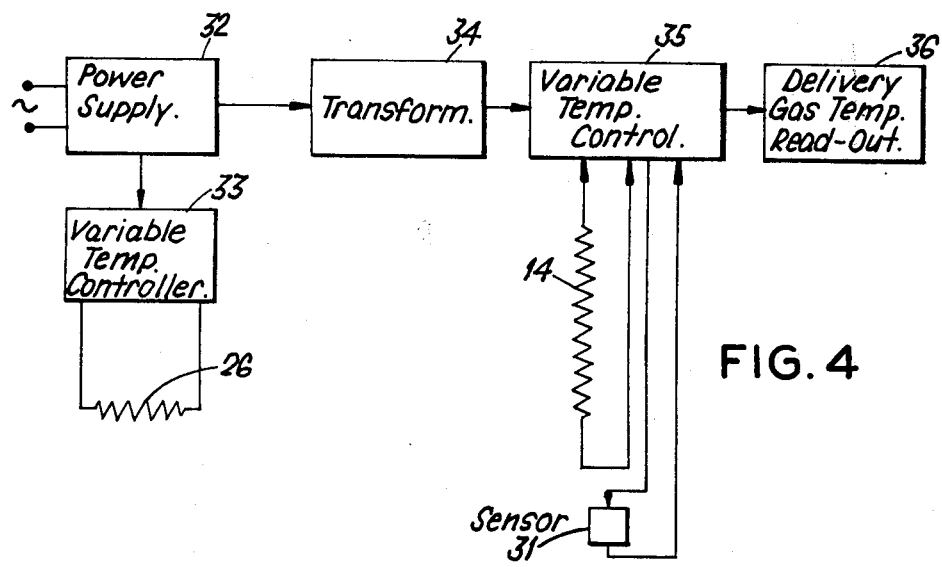
FIG. 4 is a schematic representation of electrical circuitry associated with the apparatus.

The control circuitry associated with the above described apparatus is shown in FIG. 4 and it includes a power supply 32 which may be a mains supply. The power supply is connected through an adjustable temperature controller 33 to the air/water heater 26, and through a transformer 34 to a variable temperature controller 35. The temperature controller 35 provides low voltage energising current to the heater coil 14, the current level being selectively variable in accordance with the delivered gas temperature to effect a required heat transfer to gas passing through the delivery line 25 so that the delivered gas temperature is maintained sensibly constant at the desired level. Operation of the controller 35, to provide for current variation, takes place automatically when the apparatus is in use, the automatic adjustment being controlled by the sensor 31 and being completely independent of the temperature control of the humidifier chamber effected by the heater 26.

A delivery gas temperature read-out device 36, which is controlled by the sensor 31, is incorporated in the circuit.

In operation of the device above described, the heater 14 operates automatically, as above mentioned to provide for a desired gas temperature $T_2$ at the delivery end of the line 25. Also, the heating level of the heater coil 26 is adjusted and set to effect heating of the gas passing through the evaporating chamber 16 to a temperature $T_1$ by the time it leaves the chamber to provide for a desired humidity level $W_2$ at the delivery point temperature $T_2$ which is lower than $T_1$. As is clear from FIG. 4, the control of the heater coil 26 is totally independent of the temperature sensor 31 which regulates only the temperature of the resistance coil 14. By the use of separate control loops for regulating the temperatures of the coils 14 and 26, the gas temperature regulation is effected quickly and efficiently as the relatively slow response of the water in the evaporation chamber 16 to heat applied by the coil 26 has no effect on the response time of the gas temperature control loop.

The cage 21 containing the float 20 is of cup shape. Its portion above the water level is dry and serves to heat the gas flowing around it without humidifying it. This ensures that the gas is never fully saturated when leaving the chamber 16. As previously stated, it is a feature of the invention that the gases leaving the evaporation chamber 16 must not be 100% saturated because they are at a temperature above that required by the patient and were they to be 100% saturated any subsequent temperature drop along the delivery line would result in condensation therein. This should be contrasted with prior art apparatus where special evaporative surfaces are introduced into the gas flow path in the humidification chamber for the opposite reason, namely, to increase the humidification of the gases flowing therethrough. It is a simple matter to remove the cage 21 and float 20 from the chamber 16 when cleaning and servicing has to be carried out and all the interior surfaces of the chamber 16 are then readily accessible.

Figure 5:
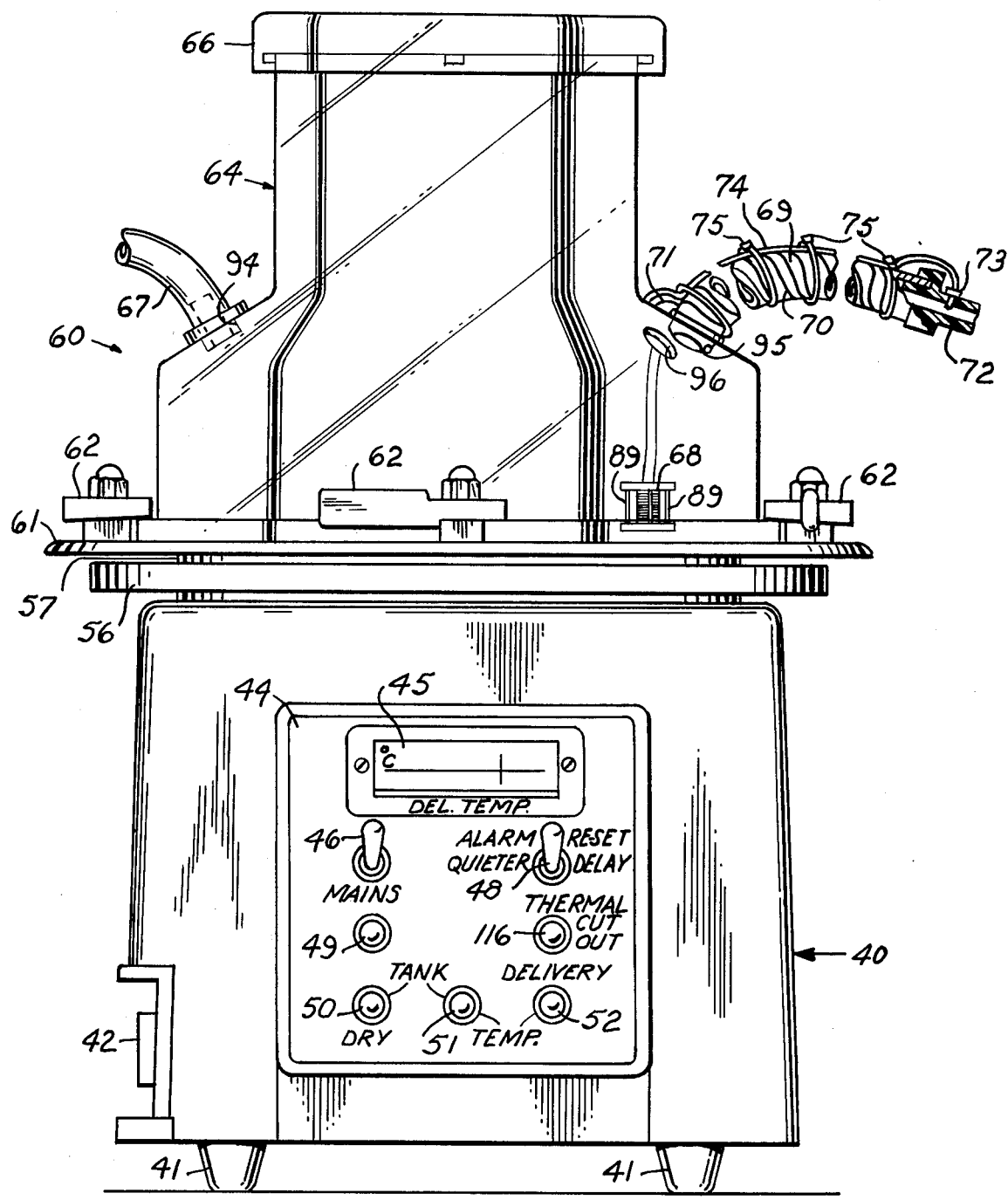
FIG. 5 shows a modified humidifier tank on a stand containing electrical control circuitry, parts associated with the tank such as the delivery hose being partly broken away.

The apparatus shown in FIG. 5 comprises a stand 40 having legs 41 and an electrical plug socket 42. It has mounted within it control circuitry, to be described in more detail later, and which is provided with a control panel 44 on one face of the stand. The panel 44 has a meter 45 from which the temperature of gas delivered to the patient can be read; a mains supply ON/OFF switch 46; a three-position alarm switch 48; and five indicating lamps 49, 50, 51, 52 and 116 which are associated with different parts of the electrical circuitry and individually light up, simultaneously with an audible alarm being given, in the event of a predetermined hazardous condition developing. The lamp 49 indicates the presence of mains supply, the lamp 50 indicates the water level in a humidifier chamber being beneath a chosen level, the lamp 51 indicates the water temperature in the humidifier falling outside predetermined limits, and the lamp 52 indicates that the delivery temperature has passed outside of a predetermined range. The indicator lamp 116 is provided to signify that a tank heater coil on the stand has been switched out of a circuit by an independent non-cycling thermal cut-out located adjacent the heating coil.

A support flange 56 has a thin removable ceramic ring 57 resting on it and encircling the tank heater coil (not shown). In the absence of the humidifier tank the heater coil, which is arranged in the horizontal plane, projects slightly above the surface of the ceramic ring 57 so that, when the humidifier tank is placed in position, it presses the coil lightly downwards against the thrust of its support springs which ensures a good physical contact between the surface of the coil and the underside of the humidifying tank.

The humidifying tank is shown at 60 and is of composite construction. Its underside is provided by a flat stainless steel plate 61 held by turn-buckles 62 to a rim flange 63 provided around the underside of a polycarbonate-transparent moulding 64 described in more detail later with reference to FIGS. 6 to 8. The tank 60 is closed by a bayonet fitting top cap 66 and has top openings for attaching to it an air supply pipe 67, a water temperature level sensing element 68, and a delivery hose 69 which is made of flexible material and is encircled by a heating coil 70. Electrical connections 71 extend from the end of the coil 70 adjacent the tank 60 to the control circuitry in the stand 40. The end of the hose 69 remote from the tank 60 is provided with a detachable plastics nozzle 72 containing a gas temperature sensing device 73 which is connected by a cable 74 to the control circuitry in the stand 40. Removable plastics clips 75 hold the cable 74 against the outside wall of the hose 69.

Figure 6:
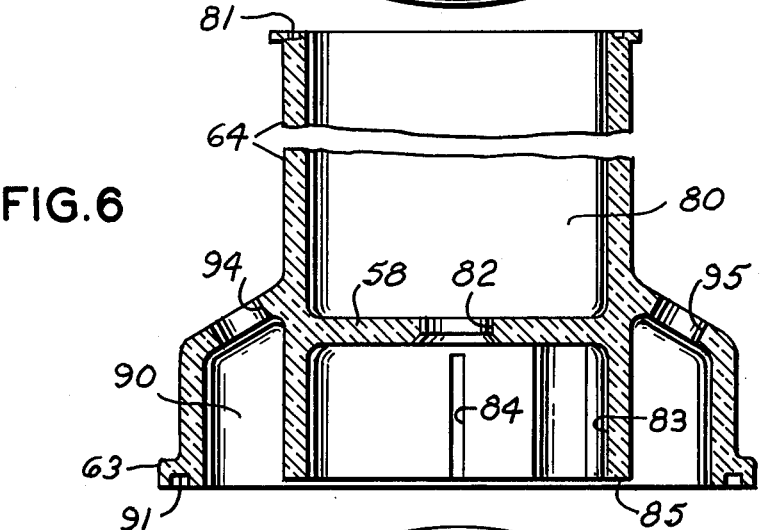
FIG. 6 is a vertical section through the tank with the base removed.

The tank 60 is shown in more detail in FIG. 6 and comprises a transparent upper cylindrical chamber 80 providing a reservoir for water the level of which is easily visible, and having a groove 81 around its top rim for the reception of an O-ring seal which is located beneath the top cap 66. The reservoir 80 has a floor 58 containing a central opening 82 through which water is supplied, in controlled manner, to a cylindrical float chamber 83 beneath. The wall of the float chamber is provided with a vertical slot 84 and its lower rim 85 terminates above the lower rim of the peripheral flange 63 so as not to touch the bottom of the tank 60. This allows water to flow from the float chamber 83 into an annular humidifying chamber 90 which encircles the float chamber 83. An annular groove 91 in the peripheral flange 63 enables a sealing O-ring to be located between the flange and the plate 61 so that a watertight seal is formed between them. The upper region of the humidifier chamber 90 is provided with an inlet port 94 for admitting air, and an exit port 95 for exhausting humidified air from the chamber 90 in which it flows along the two parallel arcuate paths indicated by the arrows shown in broken outline in FIG. 8. Alongside the outlet port 95 is a further opening 96 which receives the water temperature level sensing element 68 shown in FIG. 5. Electrical connections (not shown) extend from the element 68 to the control circuitry in the stand 40.

Figure 7:
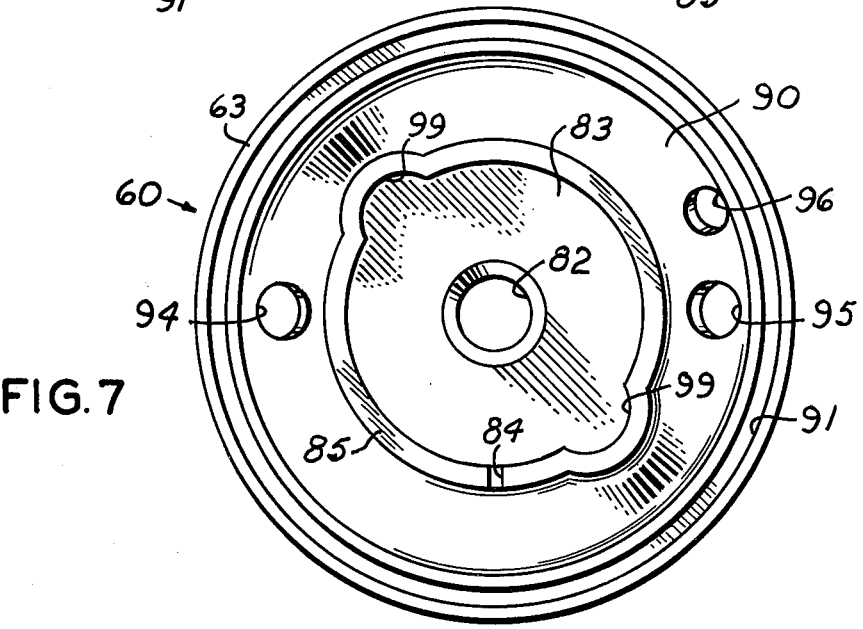
FIG. 7 is a view of the underside of the tank.

As is clearly apparent from FIG. 7, two outwardly bulging flutes 99 in the wall of the float chamber 83 facilitate finger access to the float from the underside of the moulding 64 after the base plate 61 has been removed, to make removal of the float easier.

Figure 8:
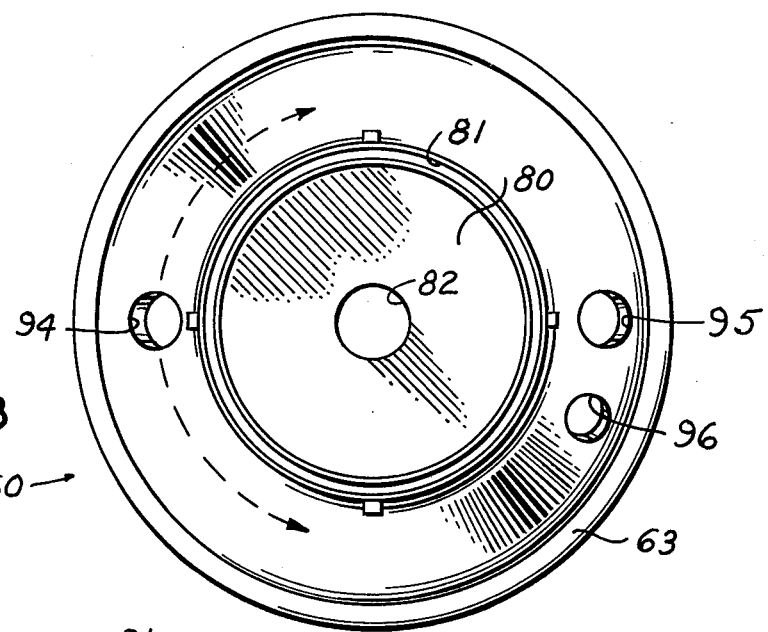
FIG. 8 is a plan view of the tank.

As is clearly apparent from FIGS. 6, 7 and 8, the polycarbonate moulding is simple to manufacture, easy to clean, and transparent.

The water temperature sensing element 68 comprises a bobbin-shaped element arranged with its axis vertical. The core of the bobbin is provided by an encapsulated wire wound temperature sensing coil and four equally spaced electrode wires 89 are arranged around the bobbin core and spaced therefrom. The electrodes 89 are arranged in pairs which are insulated from one another so that the electrical resistance between them is significantly less if they are immersed in water. Thus the element 68 serves the dual functions of indicating the water temperature in the humidifier chamber as is signified by the temperature sensing coil, and indicating the fall in level of the water in the humidifier chamber to an extent such that the electrodes 89 are no longer immersed. The increase in electrical resistance between the wires initiates a signal in the control circuitry which causes the alarm to sound and the lamp 50 to light.

The flow of water through the opening 82 may be controlled by a float valve as has already been described with reference to FIG. 3. However, it is preferred to use a presently available valve of a different construction and which forms no part of my invention. However, a few comments on the construction of the valve may assist the reader to appreciate its advantages.

The preferred water control valve, not shown, comprises a frusto-conical float locating snugly within the float chamber 83 and which is vertically movable within it. The upper end of the float is provided with an upright mushroom-shaped stud whose cylindrical shank is guided in an apertured hub of a two-part nut which fits within the opening 82. The lower part of the nut has a ring of holes which allows water, entering an intermediate chamber of the nut from above, to flow downwardly into the float chamber. The upper part of the nut screws onto the upper portion of the lower part of the nut, projecting upwardly through the aperture 82, and is provided centrally with a circular hole having a rounded rim whose radius of curvature is approximately centered on the outer corner periphery of the top part of the nut.

The mushroom head of the stud which is vertically moved by the float has a slightly larger radius towards its rim than the hole in the top part of the nut so that when the float lifts, the rounded convex surface of the mushroom head forms a continuous line seal with the rounded rim of the hole in the top part of the nut, but if the float descends, the force of surface tension provided by the line contact between the head and the hole rim is insufficient to hold the mushroom head in position and thereby reduce the sensitivity of the valve to change in water level in the float chamber. Although the above construction of valve is preferable, any other form of valve is suitable which is capable of being operated by a float and is relatively insensitive to surface tension effects on the closing surfaces of the valve. An advantage of the above described valve is that it has the necessary sensitivity and it is also capable of being removed totally from the moulding 64 and being then dismantled completely to enable cleaning of all parts to be carried out quickly and effectively.

Figure 9:
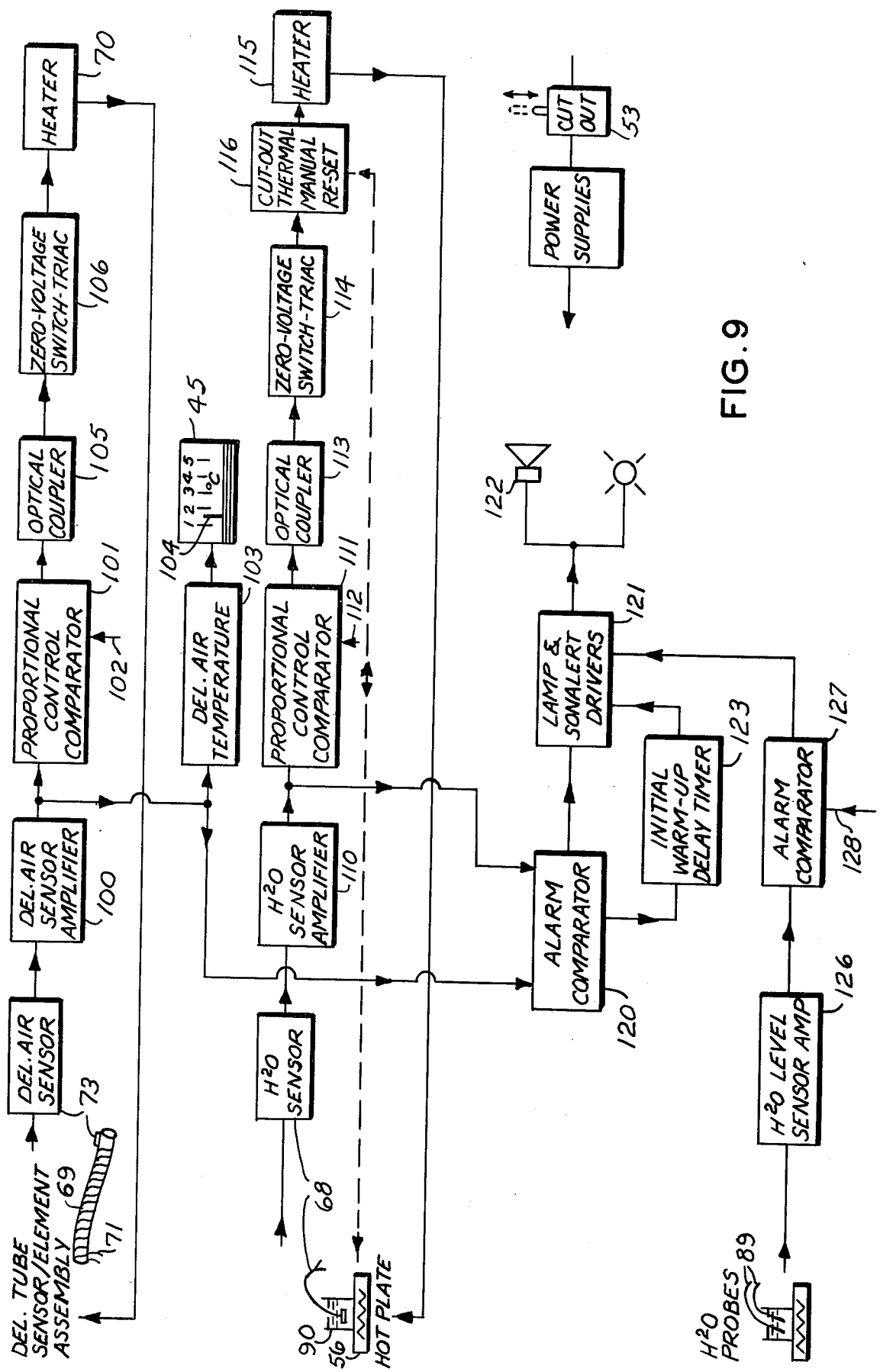
FIG. 9 is a schematic circuit diagram of control circuitry associated with the tank; and, FIG. 10 is an alarm logic circuit to assist understanding.

The electrical circuitry will now be described with reference to the block diagram shown in FIG. 9.

The circuitry, as in the previous embodiment, comprises two independently operating control loops. The first controls the temperature of the hose 69 and the second controls the temperature of the water in the humidifier chamber 90.

Turning to the first control loop this receives the signal from the sensor 73 which responds to the temperature of air delivered to the patient, and passes it through an amplifier 100. The amplifier output is fed to a proportional control comparator 101 which receives a second input 102 significant of the reference temperature which is to be maintained at the outlet nozzle 72. The output from the amplifier 100 is also fed to a signal circuit 103 which drives a pointer 104 of the meter 45.

The error signal, if such exists, between the two inputs fed to the comparator 101 is fed through an optical coupler 105, known per se, to a zero voltage Triac switch 106. This supplies power to the resistance coil 70 wound around the hose 69 at the appropriate rate to reduce any error to zero. Thus a closed loop control system is formed which does not include the water in the humidifier chamber and which therefore is far more responsive to fluctuations in temperature changes at the output nozzle 72 because there is no large inertia introduced into the closed loop by the presence of the water tank of the humidifier as is the case with some prior art systems.

The second closed loop control system is confined to controlling the temperature of the water in the humidifier chamber 90. The temperature of the water in the chamber is detected by the sensing device 68 which produces an electrical output signal fed to an amplifier 110. The amplified output is fed to a second porportional control comparator 111 which receives a reference input 112 significant of the temperature it is desired to maintain and which is found empirically. The output from the amplifier 110 is also fed to a monitoring alarm circuit forming the lower part of FIG. 9.

Any error between the temperature of the water in the humidifier chamber and the desired temperature produces an error signal which is fed from the comparator 111 through an optical coupler 113 to a zero voltage Triac switch 114. This provides an electrical power output to a radiant heater coil 115 which is resiliently pressed against the underside of the base plate 61 of the tank 60. The heater coil 115 is fed by way of the thermal cut-out switch 116 which is located in the centre of the heater coil. A cut-out power switch 53 closes when the tank 60 is placed in position on the stand 40 the switch 53 being operated by a press-button by the tank weight. In the absence of the tank 60, power is not supplied and the heater 115 is not energized. It will therefore be appreciated that the water in the humidifier chamber 90 has its temperature controlled by a closed loop-control system which is completely independent of that used to control the temperature of the gas flowing through the hose 69.

The alarm circuit comprises a comparator 120 which receives an input from each of the amplifiers 100, 110.

Figure 10:
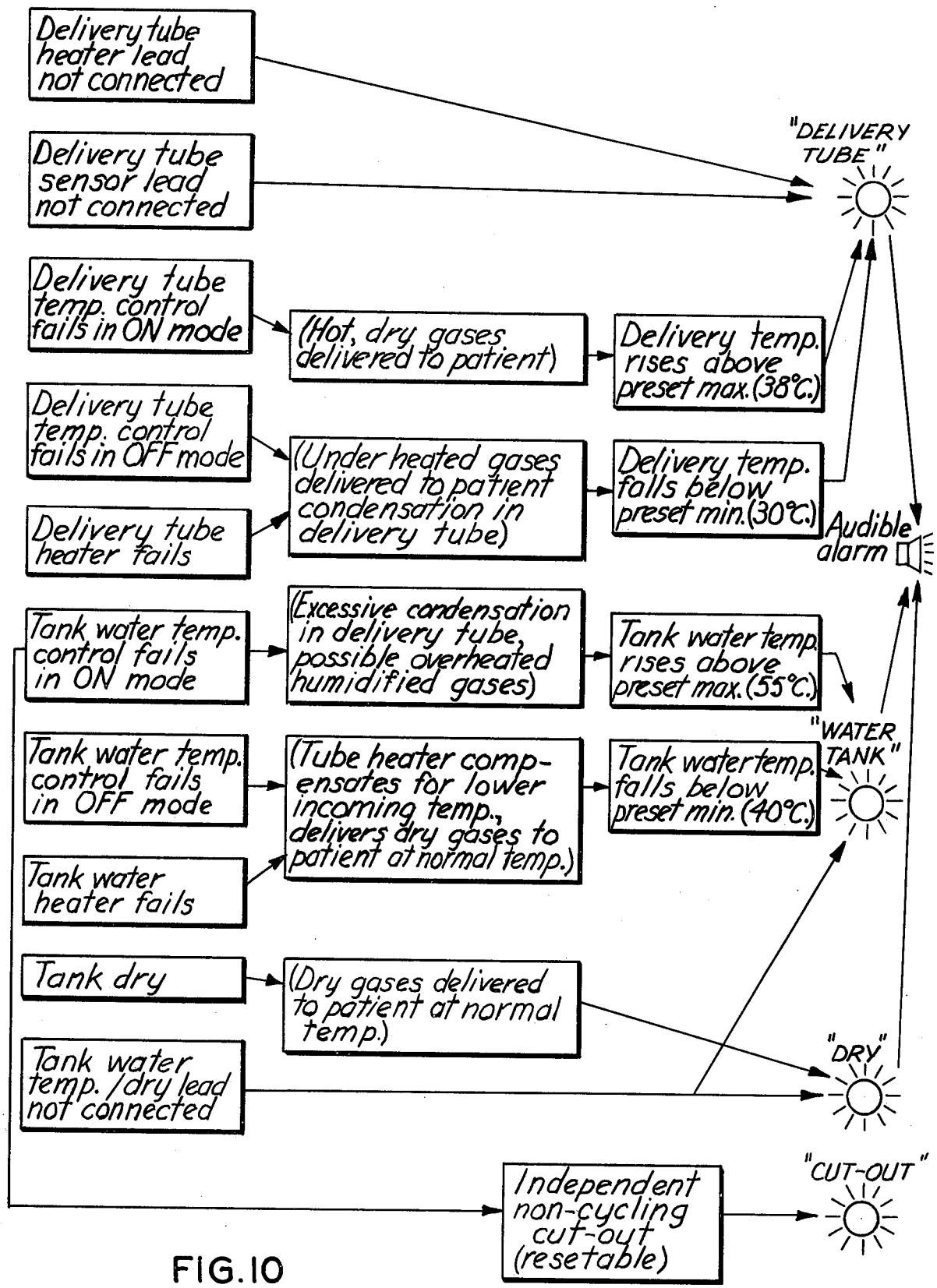

Preset controls on the comparator ensure that output signals are provided if the amplified outputs fall outside of predetermined ranges. The presence of an output signal results in the appropriate lamp of the lamp set 49 to 53 and 116 operating to indicate the system in which the fault lies. Simultaneously, the illumination of one of the lamps causes a set of driver circuits 121 to respond by illuminating the appropriate lamp and sounding an audible alarm by way of a loudspeaker 122. This alarm can be quieted by means of the tumbler switch 48 shown in FIG. 5. The logic of the alarms is set out in FIG. 10 which is believed to be self-explanatory.

During the warm-up of the apparatus to its running conditions, it is obviously undesirable for the alarms to sound and in this case a delay timer 123 operates, on switching on of the apparatus, to prevent the alarm driver circuits 121 from operating until a predetermined time has elapsed shown by experience to be sufficient for steady conditions to exist. It can be prolonged by placing the switch 48 temporarily in its "reset" position.

The alarm driver circuits 121 receive a further alarm-initiating signal if the water level in the humidifier chamber 90 falls to a level such that the four electrodes 89 are all exposed. In this case, the electrical resistance between them increases sharply and a signal is sent to a water level sensing amplifier 126. This supplies the amplified signal to a comparator 127 which receives a second input 128 providing a reference and which enables an error output signal to be generated in the event of the water level in the chamber falling to an unacceptably low condition which could arise if the float controlling the reservoir valve jammed, or, alternatively, if the reservoir of water is exhausted.

The apparatus shown in FIGS. 5 to 10 operates as follows. The cap 66 is removed and the reservoir 80 is half-filled with water. Some of this flows down into the float chamber and, via the slot 84 and the annular clearance 85, into the humidifier chamber 90. The float within the chamber rises until the valve in the opening 82 closes. The cap 66 is replaced on top of the reservoir and its bayonet fitting ensures that it forms an airtight seal. The ceramic ring 57 is placed on the flange 56 and the tank 60 is placed on the ceramic ring which provides a thermal insulation layer. The placing of the tank 60 on the stand 40 causes the cut-out switch 53 to operate to allow power to be supplied to the heaters when the mains switch 46 is thrown.

The water level sensing and temperature measuring device is mounted in the humidifier chamber 90 by way of the opening 96 which is then plugged and the electrical leads are connected to the appropriate connection points on the stand 40. Likewise, the flexible air supply hose 69 is fixed at one end to the opening 95 and the nozzle 72 is fixed to the other end. The temperature sensing element 73 is located in the nozzle 72 and the cable leading from it is clipped to the outside of the hose at spaced positions and fed with the cable 71 through the appropriate connection point on the stand 40.

The mains switch is turned on to allow the heater coil to heat the base plate 61 on the tank. The water inside the tank is raised to the temperature determined by the input 112 to the comparator 111 (see FIG. 9) and the lamps on the stand indicate when this time is reached. Simultaneously air at the desired rate is passed through the humidifier chamber 90 and flow above the surface of the water around the arcuate paths shown in FIG. 8 to the exit port 95. During their passage through the humidifier chamber the gases are heated and pick up moisture. They leave the humidifier chamber at a temperature typically in the region of 41° C and with a humidity of 80% to 85%.

The moisture laden air travels through the hose 69 to the outlet nozzle 72 and is progressively cooled at a controlled rate such that it reaches the outlet nozzle 72 at the desired temperature, typically 37° C and with a humidity of 95% to 100%. The heat imparted to the hose 69 ensures that the water vapour never cools to a level, during its passage through the hose, at which its saturation rises to 100% and rain-out subsequently occurs. In practice, the stabilized temperature of the humidifier chamber is preset such that the difference in gas temperature at the inlet and outlet of the delivery hose is sufficient to attain full saturation at the nozzle 72, but not before.

When the temperature of the gas at the nozzle 72 reaches the correct level indicated by the meter 45, the apparatus is operating in a steady condition for use.

As moisture is drawn from the humidifier, the water level in the chamber falls and the float descends in the float chamber to allow fresh water from the reservoir to enter. Fluctuations in water temperature consequently occur in the float chamber but these do not affect the transfer of water vapour to the air because the air travels around and not through the float chamber. The slot in the side wall of the float chamber ensures that the water level in both the humidifier and float chamber is constant.

Should the float stick in the open position and there is sufficient water in the reservoir chamber, the reservoir will discharge into the float chamber until the water level in the humdifier chamber is just beneath the level of the air exit port 95. The float chamber is then full of water and, as the reservoir is sealed by the top cap 66, no further water can flow through the open valve 82. It will be noticed from FIG. 6 that, even in this full condition, there are still parallel arcuate flow paths between the air entry and air exit ports and that there is no danger of water flooding through the hose as long as the humidifier tank remains substantially upright. A further advantage obtained by sealing the reservoir 80 is that atmospheric contamination of the gases passing through the tank, is prevented or reduced to a very low level of risk indeed.

After the apparatus has been used, it is simple to clean. The humidifier tank and nozzle are disconnected from the hose and the cable clips are undone so that the hose can be sterilized. The temperature probe is easily removed from the nozzle for sterilization also and all parts of the tank are readily accessible for cleaning and sterilizing after removal of the top cap and the base plate 61. The float is removable when the turnbuckles holding the base plate in position are released, and the two-part nut can be unscrewed from the aperture 82 so that they can be cleaned and sterilized also.

I claim:

1. Humidifying apparatus comprising a reservoir chamber, a float chamber located beneath said reservoir chamber, a valve between said reservoir and float chambers, a float in said float chamber operatively controlling said valve whereby liquid is admitted from said reservoir chamber to said float chamber to maintain the liquid level therein sensibly constant when the apparatus is in use, a humidifying chamber surrounding said float chamber and which contains liquid vapour, means permitting equalizing of liquid levels in said float chamber and said humidifying chamber by allowing liquid flow from the float chamber to said humidifying chamber, a gas entry port leading into the upper portion of said humidifying chamber for admitting gas which is to be humidified thereto, a humidified gas exit port remote from said gas entry port and leading from the upper portion of said humidifying chamber, a flexible hose leading from said gas exit port and for conveying the humidified gas therefrom to a point of use, a heating element extending along said flexible hose, a gas temperature sensing element located at the gas outlet end of said hose, first electrical connections extending from said temperature sensing element, second electrical connections extending from said heating element, a temperature sensor in said humidifying chamber, third electrical connections extending from said sensor, a stand, a heater in said stand for heating said humidifying chamber, control circuitry having inputs receiving the first, second and third connections respectively and controlling operation of the hose heating element and said heater, independently operating closed loop control circuits of which the first automatically controls the hose heating element in response to the output of the temperature sensing element and the second automatically controls the heater in response to the output of the temperature sensor, and alarm circuitry monitoring the first and second control loops and providing a warning if, during operation of the apparatus, any of a number of predetermined hazard conditions develop.

2. Apparatus as set forth in claim 1, in which the humidifying chamber is annular and separated by a slotted predominantly circular wall from the float chamber, said wall being sealed at its top end to the humidifying chamber so that two separate parallel arcuate gas flow paths are provided therein between said gas inlet port and said gas exit port.

3. Apparatus as set forth in claim 1, in which the reservoir is sealed when closed by a top cap and the top of the float chamber lies beneath the level of the gas exit port whereby water cannot flow from the reservoir, when closed, into the chamber to block the gas flow path therein between the gas inlet port and the gas exit port if the water level within the float chamber rises, through a valve malfunction, to the top of the float chamber.

4. Apparatus as set forth in claim 1, in which the temperature sensor is combined in a single element with electrodes between which the electrical resistance is a function of the presence or absence of water between them, such single element is removably supported within said humidifying chamber to facilitate cleaning, and fourth connections extend upwardly from the electrodes of said element to pass through closed openings in the chamber and to lead to the control circuitry to provide an alarm therefrom if the water level in the humidifying chamber falls to a level at which said electrodes are no longer immersed in water in the chamber.

5. Humidifying apparatus comprising a cylindrical water reservoir chamber, a float chamber located beneath said reservoir chamber, a valve between said reservoir and said float chambers, a float in said chamber operatively controlling said valve whereby water is admitted from said reservoir chamber to said float chamber to maintain the water level therein sensibly constant when the apparatus is in use, a humidifying chamber surrounding said float chamber and for accumulating water vapour necessary for humidification, an apertured wall separating said float chamber from said humidifying chamber and allowing water flow through the aperture to replace the water vapourized in the humidifying chamber, a metal base plate spanning across the underside of said humidifying chamber and said float chamber with a clearance between said wall and said plate, removable compressed sealing means between the under peripheral rim of the humidifying chamber and the plate, detachable clamping means holding said base plate in a position closing said humidifying chamber and providing the floor thereof, a gas entry port leading into the upper portion of said humidifying chamber for admitting gas to be humidified thereto, a humidified gas exit port remote from said gas entry port and leading from the upper portion of said humidifying chamber to convey humidified gas therefrom, a flexible hose leading from said gas exit port for conveying the humidified gas to a point of use, a heating element extending along said flexible hose, a gas temperature sensing element located at the gas outlet end of said hose, first electrical connections extending from said temperature sensing element, second electrical connections extending from said heating element, a temperature sensor in said humidifying chamber, third electrical connections extending from said sensor, a stand, a heater in said stand for heating said humidifier chamber, control circuitry having inputs receiving the first, second and third connections respectively and controlling operation of the hose heating element and said heater, first and second independently operating closed loop control circuits of which the first automatically controls the hose heating element in response to the output of the gas temperature sensing element and the second automatically controls the heater in response to the output of the temperature sensor, and alarm circuitry monitoring the first and second control loops and providing a warning if, during operation of the apparatus, any of a number of predetermined hazard conditions develop.

6. Apparatus as set forth in claim 5, wherein said reservoir chamber, said float chamber and said humidifying chamber have their walls formed by respective parts of an integrally moulded structure which also has a part extending transversely of said walls and separating the wall portion of the reservoir chamber from the wall portions of said humidifying chamber and said float chamber which are arranged one within the other.

7. Apparatus as set forth in claim 5, wherein said reservoir chamber is an upright cylinder, said float chamber is also an upright generally cylindrical chamber located beneath said reservoir chamber, a horizontally extending floor to said reservoir provides the ceiling of said float chamber and is apertured to allow a valve-controlled flow of water therethrough, said humidifying chamber is annular and encircles said float chamber and its upper end lies above the ceiling thereof, the gas inlet and gas exit ports being positioned above the level of said ceiling and in said humidifying chamber, peripheral horizontally extending surfaces are provided outside said humidifying chamber, and turnbuckles attach the base plate in position and engage said horizontally extending surfaces with a wedging action to force the base plate tightly against the underside of the humidifying chamber to form a seal therebetween.

8. Humidifying apparatus comprising a closable reservoir chamber, a float chamber located beneath said reservoir chamber, a valve between said reservoir and float chambers, a float in said float chamber operatively controlling liquid flow through said valve whereby liquid is admitted from said reservoir chamber to said float chamber to maintain the liquid level therein sensibly constant when the apparatus is in use, a humidifying chamber surrounding said float chamber and for storing water vapour for gas humidification the upper portion of said humidifying chamber being annular and extending above the level of said valve, means permitting equalizing of liquid levels by the flow of liquid from said float chamber to said humidifying chamber to replace liquid therein as it is vaporized, a gas entry port leading into said upper annular portion of said humidifying chamber for admitting gas which is to be humidified thereto, a humidified gas exit port remote from said gas entry port and leading from said upper annular portion of said humidifying chamber and through which humidified gas leaves said chamber, a flexible hose leading from said gas exit port and for conveying the humidified gas therefrom to a point of use, a heating element extending along said flexible hose, a gas temperature sensing element located at the gas outlet end of said hose, first electrical connections extending from said temperature sensing element, second electrical connections extending from said heating element, a temperature sensor in said humidifying chamber, third electrical connections extending from said sensor, a stand, a heater in said stand for heating said humidifier chamber, control circuitry having inputs receiving the first, second and third connections respectively and controlling operation of the hose heating element and said heater, first and second independently operating closed loop control circuits of which the first automatically controls the hose heating element in response to the output of the gas temperature sensing element and the second automatically controls the heater in response to the output of the temperature sensor, removable clips encircling said hose and clamping to it at spaced intervals along its length said first electrical connections provided by a cable, a nozzle member provided at the end of said hose remote from said humidifying chamber, a temperature sensing probe constituting said temperature sensing element and removably fitted to said nozzle, and alarm circuitry monitoring the first and second control loops and providing a warning if, during operation of the apparatus, any of a number of predetermined hazard conditions develop.

9. Apparatus as claimed in claim 8, in which the reservoir, float and humidifying chambers have their walls formed from a unitary moulding made of transparent polycarbonate material, a base plate detachably attached to provide the floors of the float and humidifying chambers is made of metal, the control circuitry and water heater are provided in the stand, sealing means in compression are provided between the base plate and the outside wall of the humidifying chamber to provide a watertight seal therebetween whereas an annular gap spaces the base plate beneath the under rim of the float chamber wall so that water can circulate through the gap from the float chamber to the humidifying chamber, and the underside of the base plate is thermally insulated from a top surface of the stand on which is carried the weight of the chambers and their contents.

* * * * *

UNITED STATES PATENT AND TRADEMARK OFFICE
CERTIFICATE OF CORRECTION

PATENT NO. : 4,051,205
DATED : September 27, 1977
INVENTOR(S) : Graham Cameron Grant It is certified that error appears in the above-identified patent and that said Letters Patent are hereby corrected as shown below:

On the cover sheet, left column, the inventor's address should read-- 205 Wigram Road, Glebe, N.S.W. 2037, Australia--.

Signed and Sealed this

Third Day of January 1978

[SEAL]

Attest:

RUTH C. MASON
*Attesting Officer*

LUTRELLE F. PARKER
*Acting Commissioner of Patents and Trademarks*